US012758524B2

(12) United States Patent
Ohshima et al.

(10) Patent No.: US 12,758,524 B2
(45) Date of Patent: Oct. 13, 2026

(54) PROPHYLACTIC OR THERAPEUTIC DRUG FOR PARKINSON'S DISEASE

(71) Applicant: Kyowa Pharma Chemical Co., Ltd., Takaoka (JP)

(72) Inventors: Etsuo Ohshima, Toyama (JP); Shoichiro Tomonaga, Toyama (JP); Takahiro Isobe, Toyama (JP)

(73) Assignee: Kyowa Pharma Chemical Co., Ltd., Takaoka (JP)

( * ) Notice: Subject to any disclaimer, the term of this patent is extended or adjusted under 35 U.S.C. 154(b) by 350 days.

(21) Appl. No.: 18/572,109

(22) PCT Filed: Jul. 5, 2022

(86) PCT No.: PCT/JP2022/026755

§ 371 (c)(1),
(2) Date: Dec. 19, 2023

(87) PCT Pub. No.: WO2023/282269

PCT Pub. Date: Jan. 12, 2023

(65) Prior Publication Data

US 2024/0293359 A1 Sep. 5, 2024

(30) Foreign Application Priority Data

Jul. 8, 2021 (JP) ................................ 2021-113378

(51) Int. Cl.
*A61K 31/385* (2006.01)
*A61K 45/06* (2006.01)

(52) U.S. Cl.
CPC ............ *A61K 31/385* (2013.01); *A61K 45/06* (2013.01)

(58) Field of Classification Search
CPC .. A61K 31/164; A61K 31/198; A61K 31/385; A61K 45/06; A61P 25/16; A61P 43/00; C07D 341/00
See application file for complete search history.

(56) References Cited

U.S. PATENT DOCUMENTS

| | | | |
|---|---|---|---|
| 2019/0151270 A1 | 5/2019 | Ashby | |
| 2020/0079818 A1 | 3/2020 | Fujimoto et al. | |
| 2023/0192604 A1 | 6/2023 | Tomonaga et al. | |
| 2023/0331692 A1 | 10/2023 | Tomonaga et al. | |

FOREIGN PATENT DOCUMENTS

| | | |
|---|---|---|
| CA | 2166383 A1 | 1/1995 |
| CN | 111320603 A | 6/2020 |
| CN | 111699023 A | 9/2020 |
| EP | 4 194 437 A1 | 6/2023 |

(Continued)

OTHER PUBLICATIONS

Martinez-Banaclocha (Antioxidants, 2023, 12, 1373 pp. 1-31) (Year: 2023).*

(Continued)

*Primary Examiner* — Savitha M Rao
(74) *Attorney, Agent, or Firm* — Leydig, Voit & Mayer, Ltd.

(57) ABSTRACT

Disclosed is a prophylactic or therapeutic drug for Parkinson's disease, which comprises a trisulfide compound and is characterized by being administered in combination with a drug that is used for a dopamine supplementation therapy.

20 Claims, 4 Drawing Sheets

(56) References Cited

FOREIGN PATENT DOCUMENTS

| | | | |
|---|---|---|---|
| JP | 2019-511537 | A | 4/2019 |
| WO | WO 2006/043532 | A1 | 4/2006 |
| WO | WO 2018/117186 | A1 | 6/2018 |
| WO | WO 2020/158894 | A1 | 8/2020 |
| WO | WO 2021/054149 | A1 | 3/2021 |
| WO | WO 2021/200487 | A1 | 10/2021 |
| WO | WO 2021/231476 | A1 | 11/2021 |
| WO | WO 2022/045052 | A1 | 3/2022 |
| WO | WO 2022/045212 | A1 | 3/2022 |

OTHER PUBLICATIONS

Borah et al. (Medical Hypotheses 79 (2012) 271-273 (Year: 2012).*

The International Bureau of WIPO, International Preliminary Report on Patentability in International Application No. PCT/JP2022/026755 (Jan. 18, 2024).

Abdin et al., "Mechanism of the neuroprotective role of coenzyme Q10 with or without L-dopa in rotenone-induced parkinsonism", *Neuropharmacology*, vol. 55, No. 8, pp. 1340-1346 (Dec. 1, 2008).

Shoulson I., "Deprenyl and tocopherol antioxidative therapy of parkinsonism (DATATOP)", *Acta Neurologica Scandinavica*, vol. 80, pp. 171-175, (Nov. 1, 1989).

Martone et al., "Parkinson's disease as a disorder of the aging", *Drug Discovery Today: Therapeutic Strategies*, vol. 2, No. 4, pp. 299-305 (Jan. 1, 2005).

Vatassery et al., "Effect of Oxidative Stress Induced by L-Dopa on Endogenous Antioxidants in PC-12 Cells", *New York Academy of Sciences*, vol. 1074, No. 1, pp. 330-336, (Sep. 6, 2006).

European Patent Office, Extended European Search Report issued in European Application No. 22837683.6 (May 7, 2025).

Akaike et al., "Cysteinyl-tRNA synthetase governs cysteine polysulfidation and mitochondrial bioenergetics", *Nature Communications*, vol. 8(1177): pp. 1-15 (2017).

Burbulla et al., "Dopamine oxidation mediates mitochondrial and lysosomal dysfunction in Parkinson's disease", *Science*; 357(6357): 1255-1261 (2017).

Gille et al., "Iron-dependent functions of mitochondria—relation to neurodegeneration", *Journal of Neural Transmission*, vol. 118(3): 349-359 (2011).

Ida et al., "Reactive cysteine persulfides and S-polythiolation regulate oxidative stress and redox signaling", *Proceedings of the National Academy of Sciences of the United States of America*, vol. 111(21): 7606-7611 (2014).

Lao et al., "Intranasal and Subcutaneous Administration of Dopamine D3 Receptor Agonists Functionally Restores Nigrostriatal Dopamine in MPTP-Treated Mice", *Neurotox Res.*, vol. 24(4): 523-531 (2013).

Smeyne et al., "COVID-19 Infection Enhances Susceptibility to Oxidative Stress- Induced Parkinsonism", *Movement Disorders*, vol. 37(7): 1394-1404 (2022).

Zhang et al., "Enhanced Cellular Polysulfides Negatively Regulate TLR4 Signaling and Mitigate Lethal Endotoxin Shock", *Cell Chemical Biology*, vol. 26: 686-698 (2019).

Japan Patent Office, International Search Report issued in International Application No. PCT/JP2022/026755 (Aug. 30, 2022).

Nikolova et al., "Reducing Oxidative Toxicity of L-Dopa in Combination With Two Different Antioxidants: An Essential Oil Isolated from Rosa Damascena Mill., and Vitamin C," Toxicology Reports, 6: 267-271 (2019).

Zhou et al., "Roles of Glutathione (GSH) in Dopamine (DA) Oxidation Studied by Improved Tandem HPLC Plus ESI-MS," Neurochemical Research, 34: 316-326 (2009).

* cited by examiner

PROPHYLACTIC OR THERAPEUTIC DRUG FOR PARKINSON'S DISEASE

TECHNICAL FIELD

The present invention relates to a prophylactic or therapeutic agent for Parkinson's disease.

BACKGROUND ART

Parkinson's disease is a neurodegenerative disease that develops caused by dopaminergic neurons in the substantia nigra being selectively damaged, and that is diagnosed based on movement symptoms such as, primarily, bradykinesia, tremor, and muscle rigidity. The basis of treatment for Parkinson's disease is dopamine replacement therapy. However, there are therapeutic problems such that the amount of drugs administered required to obtain therapeutic effects gradually increases, or side effects due to dopamine replacement therapy appear, and therefore, development of a novel therapeutic agent has been expected.

In recent years, it has been reported that the deterioration of balance of the concentration of intracellular iron ions causes intracellular mitochondrial dysfunction and promoted production of reactive oxygen species (Non Patent Literature 1), leading to abnormal cell functions. In addition, when the intracellular redox balance is modulated, lipid oxidation reactions in which iron ions are involved are promoted, and eventually ferroptosis, which is a phenomenon that induces cell death from disruption of cell membrane function, receives attention.

On the other hand, a possibility that healthy and social activity impairment derived from other diseases may be aggravated caused by infectious diseases has attracted attention. For Parkinson's disease as well, a possibility that when a patient is infected with the new corona virus (SARS-CoV-2), effects of oxidative stress may enhance, and the damage to dopamine-expressing neurons may exacerbate has been reported (Non Patent Literature 2).

It has also been reported that oxidation reaction accelerated in the presence of iron ions is deeply involved also in pathogenesis and progression of Parkinson's disease. It has been pointed out that, while dopamine, neurotransmitter, has a catechol structure and originally has chemical properties which are susceptible to oxidation, the oxidation is further accelerated in the presence of iron ions. It has been pointed out that the oxidation of dopamine is a cause of loss of dopamine, and further, a dopamine oxidant produced in vivo polymerizes and forms insoluble neuromelanin, leading to a possibility of being involved in pathogenesis. In addition, it has been pointed out that the dopamine oxidant induces degeneration of α-synuclein and formation of aggregate thereof, which is involved in pathogenesis and aggravation of Parkinson's disease (Non Patent Literature 3).

Polysulfides such as glutathione trisulfide (GSSSG) are converted in vivo into reactive sulfur species such as glutathione persulfide (GSSH). It has been reported that the reactive sulfur species have potent antioxidant effect, and may have physiological function such as anti-aging (e.g., Non Patent Literatures 4 and 5). Further, as production methods of GSSSG, a method described in Patent Literature 1 is known.

Since it is desirable that drugs used for Parkinson's disease be highly efficiently delivered to nigrostriatal dopamine neurons in the brain, and nasal drop administration can avoid so-called first-pass metabolism, and directly deliver the drugs to the brain, the nasal drop administration attracts attention as an administration method for relatively increasing the concentration in the brain (Non Patent Literature 6). On the other hand, since the concentrations of the drugs that can be administered by nasal drop administration are limited, and in consideration of reducing burden on patients with medication intake, it is desirable that the drugs used for nasal trop administration can be administered as a solution and be without irritating. For example, a compound that is highly water-soluble, and free of ionizable functional group or ionically neutral is inferred as a suitable drug.

CITATION LIST

Patent Literature

Patent Literature 1: International Publication No. 2018/117186.

Patent Literature 2: International Publication No. 2022/045212.

Patent Literature 3: International Publication No. 2022/045052.

Patent Literature 4: International Publication No. 2021/200487.

Non Patent Literature

Non Patent Literature 1: Gille and Reichmann, "Iron-dependent functions of mitochondria-relation to neurodegeneration", J Neural Transm (Vienna), 2011, 118 (3):349-59.

Non Patent Literature 2: Smeyne et al., "COVID-19 infection enhances susceptibility to oxidative-stress induced parkinsonism" Mov Disord. 2022 May 17. doi: 10.1002/mds.29116. Online ahead of print.

Non Patent Literature 3: Burbulla et al., "Dopamine oxidation mediates mitochondrial and lysosomal dysfunction in Parkinson's disease", Science, 2017, 22; 357(6357):1255-1261.

Non Patent Literature 4: Ida et al, "Reactive cysteine persulfides and S-polythiolation regulate oxidative stress and redox signaling", PNAS, 2014, 111(21): 7606-7611.

Non Patent Literature 5: Akaike et al, "Cysteinyl-tRNA synthetase governs cysteine polysulfidation and mitochondrial bioenergetics", Nat. Commun., 2017, 8(1): 1177.

Non Patent Literature 6: Lao et al., "Intranasal and subcutaneous administration of dopamine D3 receptor agonists functionally restores nigrostriatal dopamine in MPTP-treated mice", Neurotox Res. 2013 November; 24(4):523-31.

SUMMARY OF INVENTION

Technical Problem

Any drug that suppresses dopamine oxidation accelerated in the presence of iron ions, and thereby suppresses a lack of dopamine has not been known. The present inventors have considered that by combining a compound having such effects with dopamine replacement therapy, there are a possibility to enhance therapeutic effects of the dopamine replacement therapy and a possibility to reduce the amount of a drug used for the dopamine replacement therapy to be administered, and thereby enabling the improvement of QOL of patients due to reduced side effects and the like. That is, an object of the present invention is to search for a compound having such effects and to provide a prophylactic or therapeutic agent for Parkinson's disease.

Solution to Problem

The present inventors have found that glutathione trisulfide, lipoic acid trisulfide, pantethine trisulfide, and N,N'-diacetyl-L-cysteine trisulfide suppress dopamine oxidation reaction accelerated in the presence of iron ions, and completed the present invention. The present invention provides the following [1] to [64].

[1] A prophylactic or therapeutic agent for Parkinson's disease, comprising a trisulfide compound, wherein the agent is administered in combination with a drug used for dopamine replacement therapy, wherein the trisulfide compound is glutathione trisulfide or a pharmaceutically acceptable salt thereof, a compound represented by Formula (1):

(1)

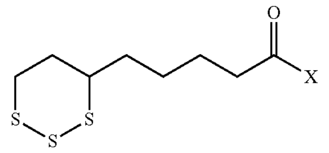

wherein X represents —$OR^1$ or —$NR^2R^3$, $R^1$ represents a hydrogen atom or an alkyl group having 1 to 6 carbon atoms, $R^2$ and $R^3$ each independently represent a hydrogen atom or an alkyl group having 1 to 6 carbon atoms, the alkyl group optionally having one or more substituents selected from the group consisting of an amino group and a carboxy group (hereinafter, also described as Compound (1)), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[2] A prophylactic or therapeutic agent comprising a drug used for dopamine replacement therapy, wherein the agent is administered in combination with a trisulfide compound, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[3] The prophylactic or therapeutic agent according to [1] or [2], wherein the trisulfide compound and the drug used for dopamine replacement therapy are administered simultaneously or separately.

[4] A prophylactic or therapeutic agent for Parkinson's disease, comprising: a trisulfide compound; and a drug used for dopamine replacement therapy, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[5] The prophylactic or therapeutic agent according to any one of [1] to [4], wherein the trisulfide compound is glutathione trisulfide or a pharmaceutically acceptable salt thereof.

[6] The prophylactic or therapeutic agent according to [5], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[7] The prophylactic or therapeutic agent according to [5], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[8] The prophylactic or therapeutic agent according to any one of [1] to [4], wherein the trisulfide compound is lipoic acid trisulfide or a pharmaceutically acceptable salt thereof.

[8-2] The prophylactic or therapeutic agent according to any one of [1] to [4], wherein the trisulfide compound is pantethine trisulfide or a pharmaceutically acceptable salt thereof.

[8-3] The prophylactic or therapeutic agent according to any one of [1] to [4], wherein the trisulfide compound is N,N'-diacetyl-L-cysteine trisulfide or a pharmaceutically acceptable salt thereof.

[9] The prophylactic or therapeutic agent according to any one of [1] to [8-4], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[10] A kit for preventing or treating Parkinson's disease, the kit comprising: a formulation comprising a trisulfide compound; and a formulation comprising a drug used for dopamine replacement therapy, wherein the trisulfide compound is glutathione trisulfide or a pharmaceutically acceptable salt thereof, Compound (1), a pharmaceutically acceptable salt thereof or a cyclodextrin clathrate thereof, or pantethine trisulfide or a pharmaceutically acceptable salt thereof, or N,N'-diacetyl-L-cysteine trisulfide or a pharmaceutically acceptable salt thereof.

[11] The kit according to [10], wherein the formulation comprising the trisulfide compound and the formulation comprising the drug used for dopamine replacement therapy are administered simultaneously or separately.

[12] The kit according to [10] or [11], wherein the trisulfide compound is glutathione trisulfide or a pharmaceutically acceptable salt thereof.

[13] The kit according to [12], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[14] The kit according to [12], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[15] The kit according to [10] or [11], wherein the trisulfide compound is lipoic acid trisulfide or a pharmaceutically acceptable salt thereof.

[15-2] The kit according to [10] or [11], wherein the trisulfide compound is pantethine trisulfide or a pharmaceutically acceptable salt thereof.

[15-3] The kit according to [10] or [11], wherein the trisulfide compound is N,N'-diacetyl-L-cysteine trisulfide or a pharmaceutically acceptable salt thereof.

[16] The kit according to any one of [10] to [15-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[17] A method for preventing or treating Parkinson's disease, the method comprising administering a trisulfide compound, and a drug used for dopamine replacement therapy or a pharmaceutically acceptable salt thereof to a patient in need thereof, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[18] The method according to [17], wherein the trisulfide compound and the drug used for dopamine replacement therapy are administered simultaneously or separately.

[19] The method according to [17] or [18], wherein the trisulfide compound is glutathione trisulfide or a pharmaceutically acceptable salt thereof.

[20] The method according to [19], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[21] The method according to [19], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[22] The method according to [17] or [18], wherein the trisulfide compound is lipoic acid trisulfide or a pharmaceutically acceptable salt thereof.

[22-2] The method according to [17] or [18], wherein the trisulfide compound is pantethine trisulfide or a pharmaceutically acceptable salt thereof.

[22-3] The method according to [17] or [18], wherein the trisulfide compound is N,N'-diacetyl-L-cysteine trisulfide or a pharmaceutically acceptable salt thereof.

[23] The method according to any one of [17] to [22-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[24] A drug used for dopamine replacement therapy, for use in preventing or treating Parkinson's disease, wherein the drug is administered in combination with a trisulfide compound, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[25] The drug used for dopamine replacement therapy for use according to [24], wherein the trisulfide compound and the drug used for dopamine replacement therapy are administered simultaneously or separately.

[26] The drug used for dopamine replacement therapy for use according to [24] or [25], wherein the trisulfide compound is glutathione trisulfide or a pharmaceutically acceptable salt thereof.

[27] The drug used for dopamine replacement therapy for use according to [26], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[28] The drug used for dopamine replacement therapy for use according to [26], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[29] The drug used for dopamine replacement therapy for use according to [24] or [25], wherein the trisulfide compound is lipoic acid trisulfide or a pharmaceutically acceptable salt thereof.

[29-2] The drug used for dopamine replacement therapy for use according to [24] or [25], wherein the trisulfide compound is pantethine trisulfide or a pharmaceutically acceptable salt thereof.

[29-3] The drug used for dopamine replacement therapy for use according to [24] or [25], wherein the trisulfide compound is N,N'-diacetyl-L-cysteine trisulfide or a pharmaceutically acceptable salt thereof.

[30] The drug used for dopamine replacement therapy for use according to any one of [24] to [29-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[31] A trisulfide compound for use in preventing or treating Parkinson's disease, wherein the trisulfide compound is administered in combination with a drug used for dopamine replacement therapy, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[32] The trisulfide compound for use according to [31], wherein a formulation comprising the trisulfide compound and a formulation comprising the drug used for dopamine replacement therapy are administered simultaneously or separately.

[33] The trisulfide compound for use according to [31] or [32], wherein the trisulfide compound is glutathione trisulfide or a pharmaceutically acceptable salt thereof.

[34] The trisulfide compound for use according to [33], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[35] The trisulfide compound for use according to [33], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[36] The trisulfide compound for use according to [31] or [32], wherein the trisulfide compound is lipoic acid trisulfide or a pharmaceutically acceptable salt thereof.

[36-2] The trisulfide compound for use according to [31] or [32], wherein the trisulfide compound is pantethine trisulfide or a pharmaceutically acceptable salt thereof.

[36-3] The trisulfide compound for use according to [31] or [32], wherein the trisulfide compound is N,N'-diacetyl-L-cysteine trisulfide or a pharmaceutically acceptable salt thereof.

[37] The trisulfide compound for use according to any one of [31] to [36-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[38] A combination of a trisulfide compound with a drug used for dopamine replacement therapy, for use in preventing or treating Parkinson's disease, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N-diacetyl-L-cysteine trisulfide or a pharmaceutically acceptable salt thereof.

[39] The combination according to [38], wherein a formulation comprising the trisulfide compound and a formulation comprising the drug used for dopamine replacement therapy are administered simultaneously or separately.

[40] The combination according to [38] or [39], wherein the trisulfide compound is glutathione trisulfide or a pharmaceutically acceptable salt thereof.

[41] The combination according to [40], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[42] The combination according to [40], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[43] The combination according to [38] or [39], wherein the trisulfide compound is lipoic acid trisulfide or a pharmaceutically acceptable salt thereof.

[43-2] The combination according to [38] or [39], wherein the trisulfide compound is pantethine trisulfide or a pharmaceutically acceptable salt thereof.

[43-3] The combination according to [38] or [39], wherein the trisulfide compound is N,N'-diacetyl-L-cysteine trisulfide or a pharmaceutically acceptable salt thereof.

[44] The combination according to any one of [38] to [43-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[45] Use of a drug used for dopamine replacement therapy, in the manufacture of a prophylactic or therapeutic agent for Parkinson's disease, wherein the drug is administered in combination with a trisulfide compound, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[46] The use according to [45], wherein a formulation comprising the trisulfide compound and a formulation comprising the drug used for dopamine replacement therapy are administered simultaneously or separately.

[47] The use according to [45] or [46], wherein the trisulfide compound is glutathione trisulfide or a pharmaceutically acceptable salt thereof.

[48] The use according to [47], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[49] The use according to [47], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[50] The use according to [45] or [46], wherein the trisulfide compound is lipoic acid trisulfide or a pharmaceutically acceptable salt thereof.

[50-2] The use according to [45] or [46], wherein the trisulfide compound is pantethine trisulfide or a pharmaceutically acceptable salt thereof.

[50-3] The use according to [45] or [46], wherein the trisulfide compound is N,N'-diacetyl-L-cysteine trisulfide or a pharmaceutically acceptable salt thereof.

[51] The use according to any one of [45] to [50-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[52] Use of a trisulfide compound, in the manufacture of a prophylactic or therapeutic agent for Parkinson's disease, wherein the trisulfide compound is administered in combination with a drug used for dopamine replacement therapy, wherein the trisulfide compound is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[53] The use according to [52], wherein a formulation comprising the trisulfide compound and a formulation comprising the drug used for dopamine replacement therapy are administered simultaneously or separately.

[54] The use according to [52] or [53], wherein the trisulfide compound is glutathione trisulfide or a pharmaceutically acceptable salt thereof.

[55] The use according to [54], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[56] The use according to [54], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[57] The use according to [52] or [53], wherein the trisulfide compound is lipoic acid trisulfide or a pharmaceutically acceptable salt thereof.

[57-2] The use according to [52] or [53], wherein the trisulfide compound is pantethine trisulfide or a pharmaceutically acceptable salt thereof.

[57-3] The use according to [52] or [53], wherein the trisulfide compound is N,N'-diacetyl-L-cysteine trisulfide or a pharmaceutically acceptable salt thereof.

[58] The use according to any one of [52] to [57-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

[59] Use of a combination of a drug used for dopamine replacement therapy with a trisulfide compound, in the manufacture of a prophylactic or therapeutic agent for Parkinson's disease, wherein the trisulfide compound is glutathione trisulfide or a pharmaceutically acceptable salt thereof, or Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof.

[60] The use according to [59], wherein the trisulfide compound is glutathione trisulfide or a pharmaceutically acceptable salt thereof.

[61] The use according to [60], wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

[62] The use according to [60], wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

[63] The use according to [59], wherein the trisulfide compound is lipoic acid trisulfide or a pharmaceutically acceptable salt thereof.

[63-2] The use according to [59], wherein the trisulfide compound is pantethine trisulfide or a pharmaceutically acceptable salt thereof.

[63-3] The use according to [59], wherein the trisulfide compound is N,N'-diacetyl-L-cysteine trisulfide or a pharmaceutically acceptable salt thereof.

[64] The use according to any one of [59] to [63-3], wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

Advantageous Effects of Invention

According to the present invention, there are a possibility to enhance therapeutic effects of the dopamine replacement therapy and a possibility to reduce the amount of a drug used for the dopamine replacement therapy to be administered, and thereby enabling the improvement of QOL of patients due to reduced side effects and the like.

DESCRIPTION OF EMBODIMENTS

Figure 1:
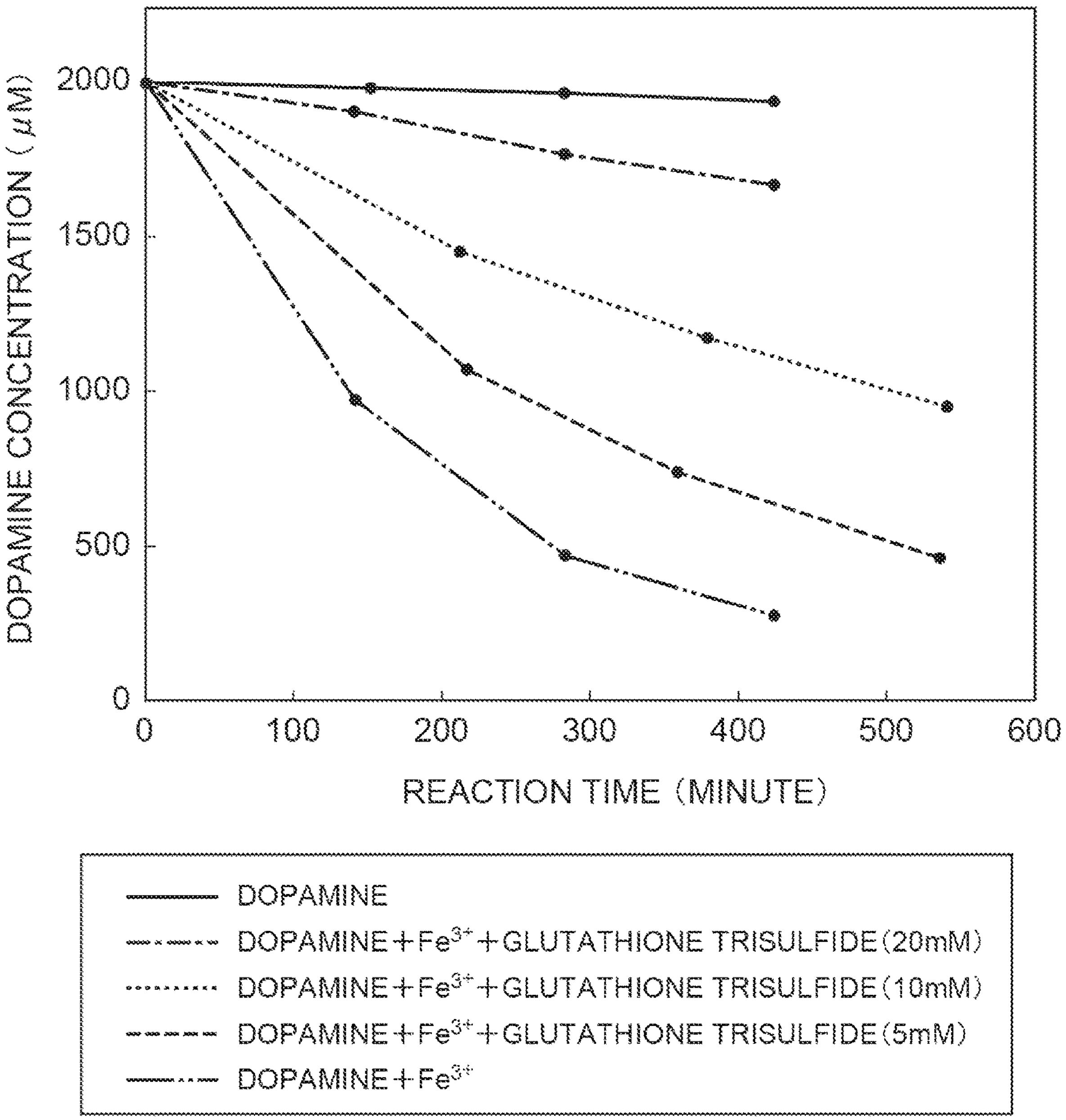
FIG. 1 is a graph showing that dopamine oxidation accelerated in the presence of iron ions is suppressed by glutathione trisulfide.

Hereinafter, the content of the present invention will be described in detail; however, the present invention is not limited to the following embodiments.

A prophylactic or therapeutic agent, and a prophylactic or therapeutic method of the present invention may be those administered or applied to a human.

A trisulfide compound used for the prophylactic or therapeutic agent of the present invention is glutathione trisulfide or a pharmaceutically acceptable salt thereof, Compound (1), a pharmaceutically acceptable salt thereof or a cyclodextrin clathrate thereof, pantethine trisulfide or a pharmaceutically acceptable salt thereof, or N,N'-diacetyl-L-cysteine trisulfide or a pharmaceutically acceptable salt thereof. The glutathione trisulfide is represented by Formula (2). The pantethine trisulfide is represented by Formula (2A). The N,N'-diacetyl-L-cysteine trisulfide is represented by Formula (2B).

(2)

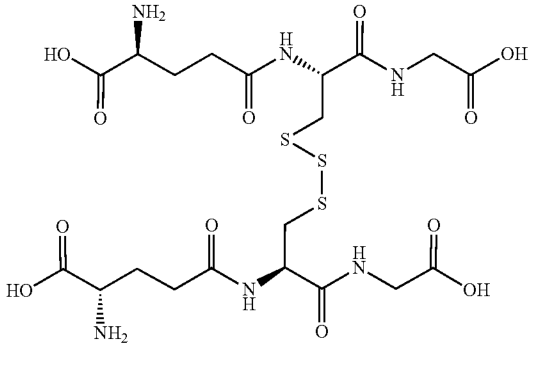

-continued (2A)

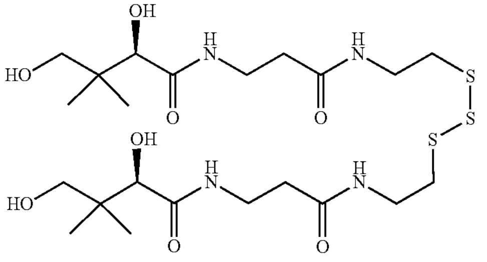

(2B)

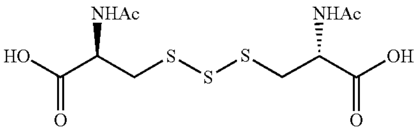

In the present invention, examples of the pharmaceutically acceptable salt can include salts with inorganic acids, such as hydrochloric acid, hydrobromic acid, sulfuric acid, nitric acid, and phosphoric acid; salts with organic acids, such as acetic acid, succinic acid, fumaric acid, maleic acid, tartaric acid, citric acid, lactic acid, stearic acid, benzoic acid, methanesulfonic acid, ethanesulfonic acid, and p-toluenesulfonic acid; salts with alkali metals, such as sodium and potassium; salts with alkali earth metals, such as calcium and magnesium; ammonium salts; and salts with amino acids, such as arginine.

It is preferable for the pharmaceutically acceptable salt of glutathione trisulfide and pantethine trisulfide to be an amino acid salt or an alkali metal salt, and more preferable to be an arginine salt or a sodium salt. It is preferable for the pharmaceutically acceptable salt of Compound (1) to be a salt with an alkali metal, and more preferable to be a sodium salt.

The glutathione trisulfide or a pharmaceutically acceptable salt thereof, Compound (1) or a pharmaceutically acceptable salt thereof, pantethine trisulfide or a pharmaceutically acceptable salt thereof, or N,N'-diacetyl-L-cysteine trisulfide or a pharmaceutically acceptable salt thereof may have a crystal polymorph, but not limited to any crystal form, and may be a single product or a mixture of any crystal form. An amorphous body is also included in the glutathione trisulfide or a pharmaceutically acceptable salt thereof, Compound (1) or a pharmaceutically acceptable salt thereof, pantethine trisulfide or a pharmaceutically acceptable salt thereof, or N,N'-diacetyl-L-cysteine trisulfide or a pharmaceutically acceptable salt thereof. An anhydride and a solvate (in particular, hydrate) are included in the glutathione trisulfide or a pharmaceutically acceptable salt thereof, Compound (1) or a pharmaceutically acceptable salt thereof, pantethine trisulfide or a pharmaceutically acceptable salt thereof, or N,N'-diacetyl-L-cysteine trisulfide or a pharmaceutically acceptable salt thereof. The glutathione trisulfide or a pharmaceutically acceptable salt thereof, Compound (1) or a pharmaceutically acceptable salt thereof, pantethine trisulfide or a pharmaceutically acceptable salt thereof, or N,N'-diacetyl-L-cysteine trisulfide or a pharmaceutically acceptable salt thereof may be a cocrystal with an amino acid (e.g., arginine).

In one embodiment, Compound (1) is a compound represented by Formula (3):

(3)

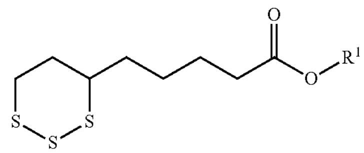

wherein $R^1$ represents a hydrogen atom or an alkyl group having 1 to 6 carbon atoms, and $R^1$ may be, for example, a hydrogen atom, a methyl group, an ethyl group, a propyl group, a butyl group, a pentyl group, or a hexyl group. Preferably, $R^1$ is a hydrogen atom, wherein the compound represented by Formula (3) is lipoic acid trisulfide represented by Formula (4).

(4)

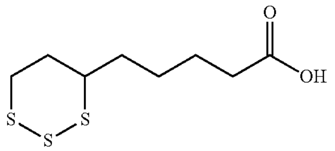

In another embodiment, Compound (1) is a compound represented by Formula (5):

(5)

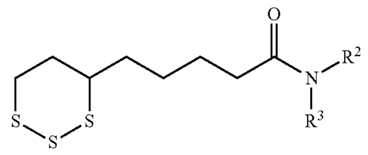

wherein $R^2$ and $R^3$ each independently represent a hydrogen atom or an alkyl group having 1 to 6 carbon atoms, the alkyl group optionally having one or more substituents selected from the group consisting of an amino group and a carboxy group. $R^1$ and $R^2$ may be a hydrogen atom, or an alkyl group such as a methyl group, an ethyl group, a propyl group, a butyl group, a pentyl group, or a hexyl group. These alkyl groups optionally have substituents of either or both of the amino group and the carboxy group. $R^1$ and $R^2$ may be, for example, a group represented by Formula (6), wherein * represents a bond. Specific examples of the compound represented by Formula (5) include a compound in which $R^2$ and $R^3$ are both hydrogen atoms, and a compound in which $R^2$ is a hydrogen atom and $R^3$ is the group represented by Formula (6).

(6)

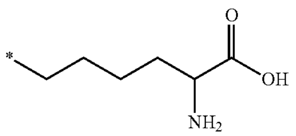

The compound represented by Formula (5) can be produced by a step of oxidizing a compound represented by Formula (5a) with an oxidant to obtain a sulfoxide compound (Step 1), and a step of causing the obtained sulfoxide compound to be reacted to a sulfur source (Step 2).

(5a)

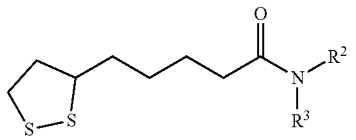

wherein $R^1$ and $R^2$ each independently represent a hydrogen atom or an alkyl group having 1 to 6 carbon atoms, the alkyl group optionally having one or more substituents selected from the group consisting of the amino group and the carboxy group.

The above production method may be conducted by performing the reactions of Step 1 and Step 2 in one pot without isolating the sulfoxide compound.

A solvent to be used in Step 1 is not particularly limited, as long as it dissolves the compound represented by Formula (5a) and the oxidant, and does not inhibit oxidation reaction. Examples of such a solvent include water, sulfuric acid aqueous solution, ethanol aqueous solution and acetonitrile aqueous solution, and it is preferably water. The amount of the solvent to be used in Step 1 can be 1 mL to 500 mL and is preferably 10 mL to 20 mL per 1 g of the compound represented by Formula (5a).

Examples of the oxidant to be used in Step 1 include potassium peroxymonosulfate (sold under the commercial name, e.g., Oxone (R)), peracetic acid, hydrogen peroxide and sodium periodate. Hydrogen peroxide may be used with the catalytic amount of methyltrioxorhenium. From the viewpoints of safety and cost, potassium peroxymonosulfate is a preferable oxidant. The amount of the oxidant to be used can be 0.8 equivalents to 2.0 equivalents and is preferably 1.0 equivalent to 1.3 equivalents per 1 equivalent of the compound represented by Formula (5a).

The reaction temperature in Step 1 can be −20° C. to 30° C. and is preferably −5° C. to 5° C.

The reaction time in Step 1 can be 5 minutes to 24 hours and is preferably 0.5 hours to 2 hours.

A solvent to be used in Step 2 is not particularly limited, as long as it dissolves the sulfoxide compound and the sulfur source, and does not inhibit subsequent reaction. Examples of such a solvent include water, sulfuric acid aqueous solution, ethanol aqueous solution and acetonitrile aqueous solution, and it is preferably water. The amount of the solvent to be used in Step 2 can be 1 mL to 500 mL and is preferably 10 mL to 20 mL per 1 g of the sulfoxide compound.

Examples of the sulfur source to be used in Step 2 include sodium sulfide, potassium sulfide, sodium hydrosulfide, potassium hydrosulfide and hydrogen sulfide. The amount of the sulfur source to be used can be 0.5 equivalents to 4.0 equivalents and is preferably 0.9 equivalents to 1.2 equivalents per 1 equivalent of the sulfoxide compound.

The reaction temperature in Step 2 can be −20° C. to 30° C. and is preferably −5° C. to 25° C.

The reaction time in Step 2 can be 10 minutes to 2 days and is preferably 0.5 hours to 2 hours.

When Step 1 and Step 2 are conducted in one pot, examples of a reaction solvent include water, sulfuric acid aqueous solution, ethanol aqueous solution and acetonitrile aqueous solution, and it is preferably water; and the amount of the solvent can be 1 mL to 500 mL and is preferably 10 mL to 20 mL per 1 g of the compound represented by Formula (5a). Examples of the oxidant to be used include potassium peroxymonosulfate, peracetic acid, hydrogen peroxide (may be used with the catalytic amount of methyltrioxorhenium) and sodium periodate, and it is preferably potassium peroxymonosulfate; and the amount of the oxidant to be used can be 0.8 equivalents to 2.0 equivalents and is preferably 1.0 equivalent to 1.3 equivalents per 1 equivalent of the compound represented by Formula (5a). Examples of the sulfur source to be used include sodium sulfide, potassium sulfide, sodium hydrosulfide, potassium hydrosulfide and hydrogen sulfide; and the amount of the sulfur source to be used can be 0.5 equivalents to 4.0 equivalents and is preferably 0.9 equivalents to 1.2 equivalents per 1 equivalent of the compound represented by Formula (5a). The reaction temperature can be −20° C. to 30° C. and is preferably −5° C. to 25° C. The reaction time can be 15 minutes to 2 days and is preferably 1 hour to 4 hours.

In addition to Step 1 and Step 2, the method may include a step of protecting functional groups such as a hydroxy group, a carbonyl group, an amino group, and a carboxy group and a step of deprotecting the protected functional groups, as needed. Protective groups, protection/deprotection reactions of these functional groups are well-known to those skilled in the art, and suitable protective groups, protection/deprotection reactions can be chosen in reference to "Greene's Protective Groups in Organic Synthesis" or the like.

The compound represented by Formula (5a) can be produced by condensing the lipoic acid and $NHR^2R^3$. Examples of solvent for condensation reaction include dichloromethane, chloroform, and tetrahydrofuran, and it is preferably tetrahydrofuran. The amount of the solvent can be 1 mL to 200 mL and is preferably 3 mL to 35 mL per 1 g of the compound represented by Formula (5a). Examples of condensing agent to be used include 1-(3-dimethylaminopropyl)-3-ethylcarbodiimide (EDC) and a salt thereof, N,N'-dicyclohexylcarbodiimide (DCC), and diisopropylcarbodiimide (DIC) (N-hydroxysuccinimide (NHS), or 1-hydroxybenzotriazole (HOBt) may be used as an additive). The amount of the condensing agent to be used can be 0.8 equivalents to 2.0 equivalents and is preferably 1.0 equivalent to 1.5 equivalents per 1 equivalent of the compound represented by Formula (5a). The reaction temperature can be −10° C. to 40° C. and is preferably 15° C. to 25° C. The reaction time can be 1 hour to 3 days and is preferably 1 hour to 24 hours.

The compound represented by Formula (5a) can also be produced by condensing the lipoic acid trisulfide and $NHR^2R^3$. The condensation conditions are the same as above.

The compound represented by Formula (3) in which $R^1$ is an alkyl group having 1 to 6 carbon atoms can be produced by a step of oxidizing a compound represented by Formula (3a) with an oxidant to obtain a sulfoxide compound (Step 1), and a step of causing the obtained sulfoxide compound to be reacted to a sulfur source (Step 2). The reaction conditions are the same as above.

(3a)

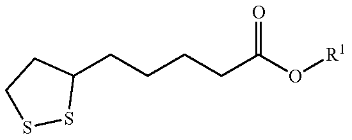

wherein $R^1$ represents a hydrogen atom or an alkyl group having 1 to 6 carbon atoms.

The compound represented by Formula (3a) can be produced by condensing the lipoic acid and $R^1OH$. The same applies as above.

The compound represented by Formula (3) in which $R^1$ is an alkyl group having 1 to 6 carbon atoms can also be produced by condensing the lipoic acid trisulfide and $R^1OH$. The condensation conditions are the same as above.

Cyclodextrin may be α-cyclodextrin, β-cyclodextrin, γ-cyclodextrin or derivatives thereof. Here, the term "derivative" means that a hydrogen atom of at least one hydroxyl group that each cyclodextrin carries is substituted with an alkyl group optionally having a substituent, or sugar. For cyclodextrin derivatives, for example, methyl-α-cyclodextrin, methyl-β-cyclodextrin, methyl-γ-cyclodextrin, dimethyl-α-cyclodextrin, dimethyl-β-cyclodextrin, dimethyl-γ-cyclodextrin, hydroxyethyl-α-cyclodextrin, hydroxyethyl-β-cyclodextrin, hydroxyethyl-γ-cyclodextrin, 2-hydroxypropyl-α-cyclodextrin, 2-hydroxypropyl-β-cyclodextrin, 2-hydroxypropyl-γ-cyclodextrin, glucosyl-α-cyclodextrin, glucosyl-β-cyclodextrin, glucosyl-γ-cyclodextrin, maltosyl-α-cyclodextrin, maltosyl-β-cyclodextrin, maltosyl-γ-cyclodextrin, sulfobutylether-β-cyclodextrin, or the like can be used.

The cyclodextrin clathrate can be produced by a step of dissolving cyclodextrin in a solvent (Step a), a step of adding Compound (1) or a pharmaceutically acceptable salt thereof to the resulting dissolved solution and stirring the mixed solution (Step b), and a step of filtering the stirred solution, washing the resulting filtrate with the same solvent as that used in Step a, freezing the filtrate to freeze-dry (Step c). Note that filtering and washing operations in Step c can be omitted.

The solvent to be used in Step a is preferably water.

The amount of the solvent to be used in Step a can be 1 to 350 ml and is preferably 1 to 80 ml per 1 g of the cyclodextrin.

In Step b, the mass ratio of cyclodextrin to Compound (1) or a pharmaceutically acceptable salt thereof can be 2 to 20, and is preferably 5 to 16.5.

The stirring temperature in Step b can be 20 to 50° C. and may be room temperature.

The stirring time in Step b can be 0.25 to 40 hours and is preferably 2 to 35 hours.

In Step b, after adding Compound (1) or a pharmaceutically acceptable salt thereof to the solution and before stirring the mixed solution, the same solvent as that used in Step a can be added thereto. Here, the amount of the solvent can be 0 to 30 ml and is preferably 0 to 20 ml per 1 g of the cyclodextrin.

The amount of the solvent to be used in Step c can be 0 to 150 ml and is preferably 0 to 20 ml per 1 g of the cyclodextrin.

The freezing temperature in Step c can be −30 to −20° C. and is preferably −20° C.

The freezing time in Step c can be 10 to 50 hours.

The freeze-drying in Step c can be performed at an absolute pressure of 20 to 100 Pa, and an external temperature of 10 to 40° C., preferably 20° C.

The freeze-drying time in Step c can be 1 to 5 days.

The pantethine trisulfide or a pharmaceutically acceptable salt thereof can be produced by the method descried in Patent Literature 3.

The N,N'-diacetyl-L-cysteine trisulfide or a pharmaceutically acceptable salt thereof can be produced by the method descried in Patent Literature 4.

Regarding the drug used for dopamine replacement therapy, for example, "Clinical Practice Guideline for Parkinson's Disease 2018" (Igaku-Shoin Ltd.) supervised by the Japanese Society of Neurology can be used as reference. In one embodiment, the drug used for dopamine replacement therapy include at least one selected from the group consisting of a dopamine precursor, a dopa-decarboxylase inhibitor, a catechol-O-methyltransferase (COMT) inhibitor, a monoamine oxidase (MAOB) inhibitor, a dopamine release accelerator, and a dopamine agonist. Examples of the dopamine precursor include levodopa (L-dopa). Examples of the dopa-decarboxylase inhibitor include carbidopa and benserazide. Examples of the COMT inhibitor include entacapone. Examples of the MAOB inhibitor include safinamide, selegiline, and rasagiline. Examples of the dopamine release accelerator include amantadine. Examples of the dopamine agonist include cabergoline, bromocriptine, pergolide, talipexole, pramipexole, ropinirole, rotigotine, and apomorphine. These drugs may be in a form of a pharmaceutically acceptable salt; and these drugs or pharmaceutically acceptable salts thereof may be crystalline or amorphous body, and anhydride or solvate (in particular, hydrate).

Specific examples of the combination of two or more drugs used for dopamine replacement therapy include concurrent use of a dopamine precursor and a dopa-decarboxylase inhibitor (e.g., concurrent use of levodopa and carbidopa, or concurrent use of levodopa and benserazide), concurrent use of a dopamine precursor, a dopa-decarboxylase inhibitor and a COMT inhibitor (e.g., concurrent use of levodopa, carbidopa and entacapone), concurrent use of a dopamine precursor and a dopamine agonist (e.g., concurrent use of levodopa and talipexole, concurrent use of levodopa and cabergoline, or concurrent use of levodopa and ropinirole), and concurrent use of a dopamine precursor and a MAOB inhibitor (e.g., concurrent use of levodopa and selegiline).

In the present invention, the phrase "administration in combination" or "concurrent use" refers to using active ingredients in combination and includes: (1) a mode of administering a single formulation comprising the drug used for dopamine replacement therapy and the trisulfide compound; and (2) a mode of separately administering the drug used for dopamine replacement therapy and the trisulfide compound as individual formulations simultaneously or at time intervals. In the case of (2), the drug used for dopamine replacement therapy may be administered first, or the trisulfide compound may be administered first. Further, in the case of (2), either of the following can be performed: (i) a mode in which the drug used for dopamine replacement therapy and the trisulfide compound are separately prepared and administered simultaneously through the same administration route; (ii) a mode in which the drug used for dopamine replacement therapy and the trisulfide compound are separately prepared and administered separately at time intervals through the same administration route; (iii) a mode in which the drug used for dopamine replacement therapy and the trisulfide compound are separately prepared and administered simultaneously through different administration routes (administered from different sites on the same patient); and (iv) a mode in which the drug used for dopamine replacement therapy and the trisulfide compound are separately prepared and administered separately at time intervals through different administration routes. Note that, in the case of (i), both of the preparations may be mixed immediately before administration.

In other words, the phrase "administration in combination" or "concurrent use" in the present invention can be said to be a usage mode of administration of either one of drugs in a state where the actions and effects of the other drug express in the patient body. That is, in the present invention, it is preferable to be a mode in which the drug used for dopamine replacement therapy and the trisulfide compound be administered so as to be present in the patient body, for example, in the blood, at the same time; and it is preferable to be a mode in which within 24 hours after one drug has been administered to the patient, the other drug is administered.

It is preferable for the amount of the drug used for dopamine replacement therapy to be administered (the amount of each drug to be administered in a case of the concurrent use of two or more drugs) to be 0.1 to 50 mg per 1 kg of body weight a day (0.1 to 50 mg/kg/day), more preferable to be 0.5 to 20 mg/kg/day, and further more preferable to be 1 to 10 mg/kg/day.

It is preferable for the amount of the trisulfide compound to be administered to be 0.5 to 800 mg per 1 kg of body weight a day (0.5 to 800 mg/kg/day), more preferable to be 1 to 400 mg/kg/day, and further more preferable to be 2 to 200 mg/kg/day.

It is preferable that the amount of the drug used for dopamine replacement therapy to be administered be 0.1 to 50 mg/kg/day and the amount of the trisulfide compound to be administered be 0.5 to 800 mg/kg/day, more preferable that the amount of the drug used for dopamine replacement therapy to be administered be 0.5 to 20 mg/kg/day and the amount of the trisulfide compound to be administered be 1 to 400 mg/kg/day, and further more preferable that the amount of the drug used for dopamine replacement therapy to be administered be 1 to 10 mg/kg/day and the amount of the trisulfide compound to be administered be 2 to 200 mg/kg/day. When the amounts of the drug used for dopamine replacement therapy and the trisulfide compound to be administered fall within this range, it is considered that higher prophylactic effects on Parkinson's disease are obtained, and further, higher therapeutic effects are exhibited. In addition, effects of further reducing side effects are also expected.

The number of administration of the drug used for dopamine replacement therapy and the trisulfide compound can be 1 to 8 times a day or 1 to 4 times a day. With the number of administration like this, the drug is considered to reduce patient's burden of taking medication and to improve medication compliance. As a result, it is expected that prophylactic or therapeutic effects of the present invention and effects of reducing side effects will further improve. When the administration of the drug is discontinued, the dose of the drugs may be gradually reduced. Examples of such a way include a method in which, while the administration of one drug is suspended, the other drug is administered.

The prophylactic or therapeutic agent for Parkinson's disease of the present invention can be administered orally as tablets, capsules, powders, granules, liquids or syrups, or parenterally as nasal drops, injections, infusions, or suppositories. The drug can be formulated in these dosage form by a known formulation technique. In a case of solids, when being formulated, a pharmacologically acceptable excipient such as starch, lactose, refined white sugar, glucose, crystalline cellulose, carboxycellulose, carboxymethylcellulose, carboxyethylcellulose, calcium phosphate, magnesium stearate, or gum arabic can be blended thereto, and if necessary, a lubricant, a binder, a disintegrant, a coating agent, a colorant or the like can be blended. In addition, in a case of liquids, a stabilizer, a dissolving aid, a suspending agent, an emulsifier, buffer, a preservative or the like can be blended.

EXAMPLES

The present invention will be described in more detail using Examples described below; however, the present invention is not limited to these.

Example 1: Suppression Test of Dopamine Oxidation Accelerated in Presence of Iron Ions For a test, dopamine hydrochloride (DA·HCl), iron(III) nitrate 9-hydrate ($Fe(NO_3)_3 \cdot 9H_2O$) as $Fe^{3+}$ source, hydrogen peroxide solution as oxidant, glutathione trisulfide 2-hydrate, lipoic acid trisulfide, pantethine trisulfide, or N,N'-diacetyl-L-cysteine trisulfide as trisulfide compound were used.

A method of preparing each substance is as follows.

10 mM DA·HCl aqueous solution: prepared by dissolving DA·HCl in purified water.

20 mM $Fe^{3+}$ solution: prepared by dissolving $Fe(NO_3)_3 \cdot 9H_2O$ in 5 mmol/L $H_2SO_4$.

40 mM glutathione trisulfide solution: prepared by dissolving glutathione trisulfide 2-hydrate in 0.2 mol/L phosphate buffer solution (pH=6.5).

40 mM lipoic acid trisulfide solution: prepared by dissolving lipoic acid trisulfide in 0.2 mol/L phosphate buffer solution (pH=6.5).

400 mM pantethine trisulfide solution: prepared by dissolving pantethine trisulfide in 0.2 mol/L phosphate buffer solution (pH==6.5).

40 mM N,N'-diacetyl-L-cysteine trisulfide: prepared by dissolving N,N'-diacetyl-L-cysteine trisulfide in 0.2 mol/L phosphate buffer solution (pH=6.5).

The pre-prepared preparation solution of each substance (mentioned above) and 0.2 M phosphate buffer solution (pH=6.5) were mixed in a 50 mL or 5 mL test tube to prepare 20 mL or 2 mL reaction solution so that each substance has the following concentration in the reaction solution.

Dopamine: 2 mmol/L $Fe^{3+}$: 2 mmol/L

Hydrogen peroxide: 1 moL/L

Glutathione trisulfide: 3 concentrations (5, 10 or 20 mmol/L)

Lipoic acid trisulfide: 2 concentrations (10 or 20 mmol/L)

Pantethine trisulfide: 3 concentrations (100, 150 or 200 mmol/L)

N,N'-diacetyl-L-cysteine trisulfide: 3 concentrations (5, 10 or 20 mmol/L)

The reaction solution was stirred at 25° C., 500 rpm for 6 to 9 hours. The dopamine concentration in the reaction solution was quantified with high performance liquid chromatography (HPLC).

The conditions for HPLC is as follows.

Detector: Ultraviolet absorptiometer (measuring wavelength: 280 nm)

Column: Inertsil ODS-2 (4.6 mm I.D.×150 mm, 5 μm)

Column temperature: constant temperature around 35° C.

Mobile phase: prepared by adding 0.2 mol/L citric acid aqueous solution to 0.2 mol/L disodium hydrogenphosphate aqueous solution to adjust to pH 3.0.

Flow rate: 0.7 mL/min

Amount infused: 20 μL

Figure 2:
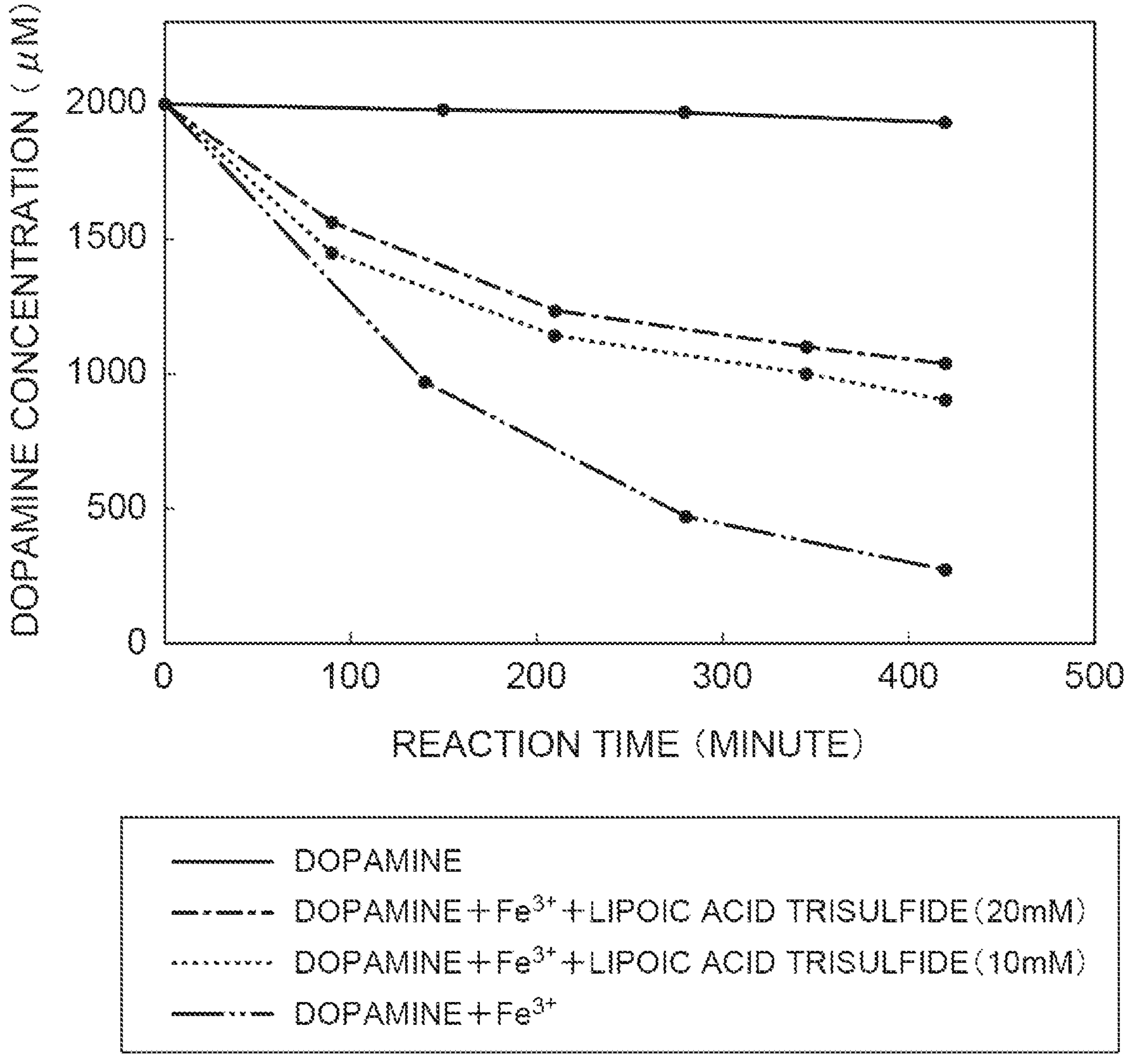
FIG. 2 is a graph showing that dopamine oxidation accelerated in the presence of iron ions is suppressed by lipoic acid trisulfide.
Figure 3:
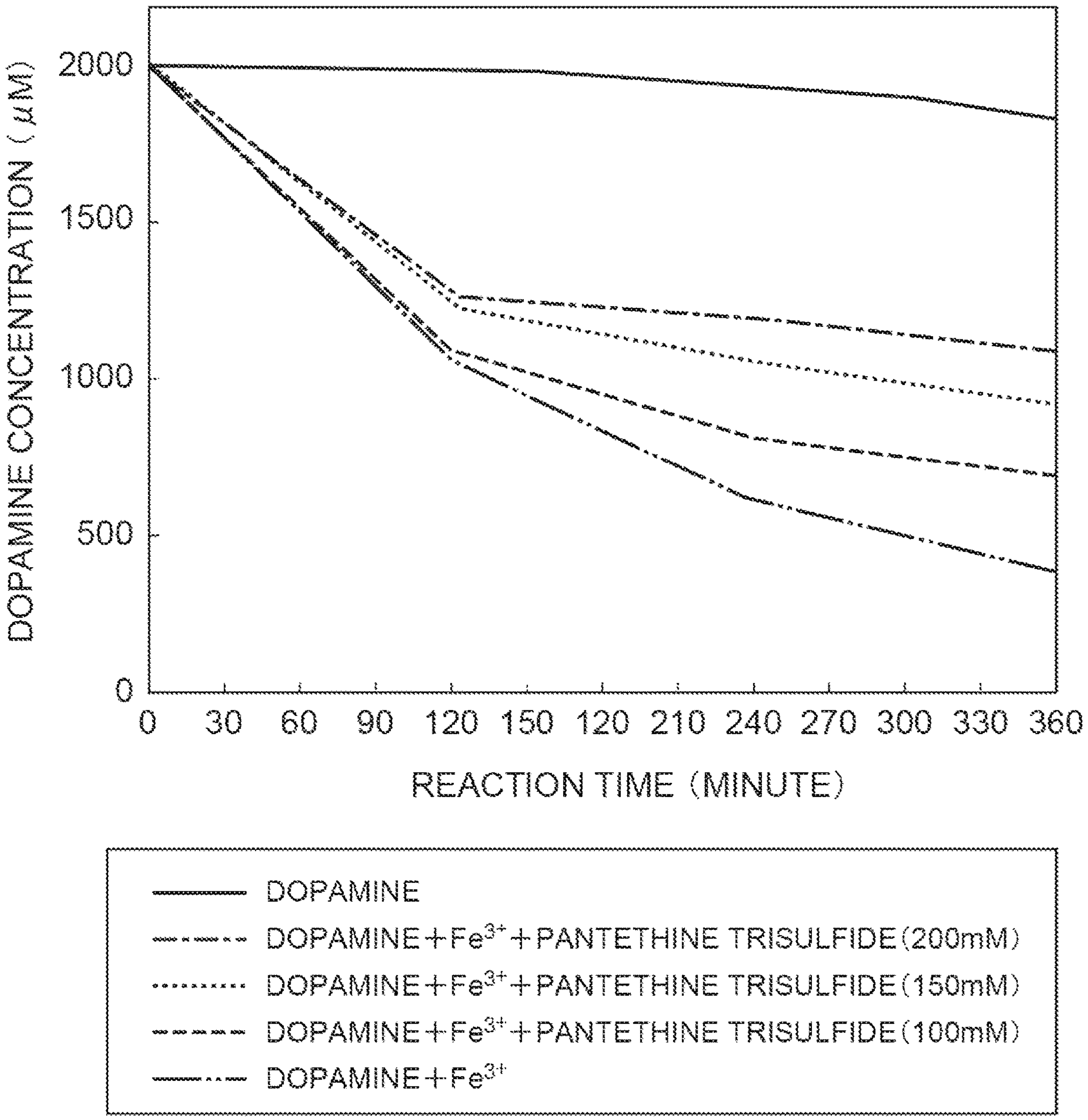
FIG. 3 is a graph showing that dopamine oxidation accelerated in the presence of iron ions is suppressed by pantethine trisulfide.
Figure 4:
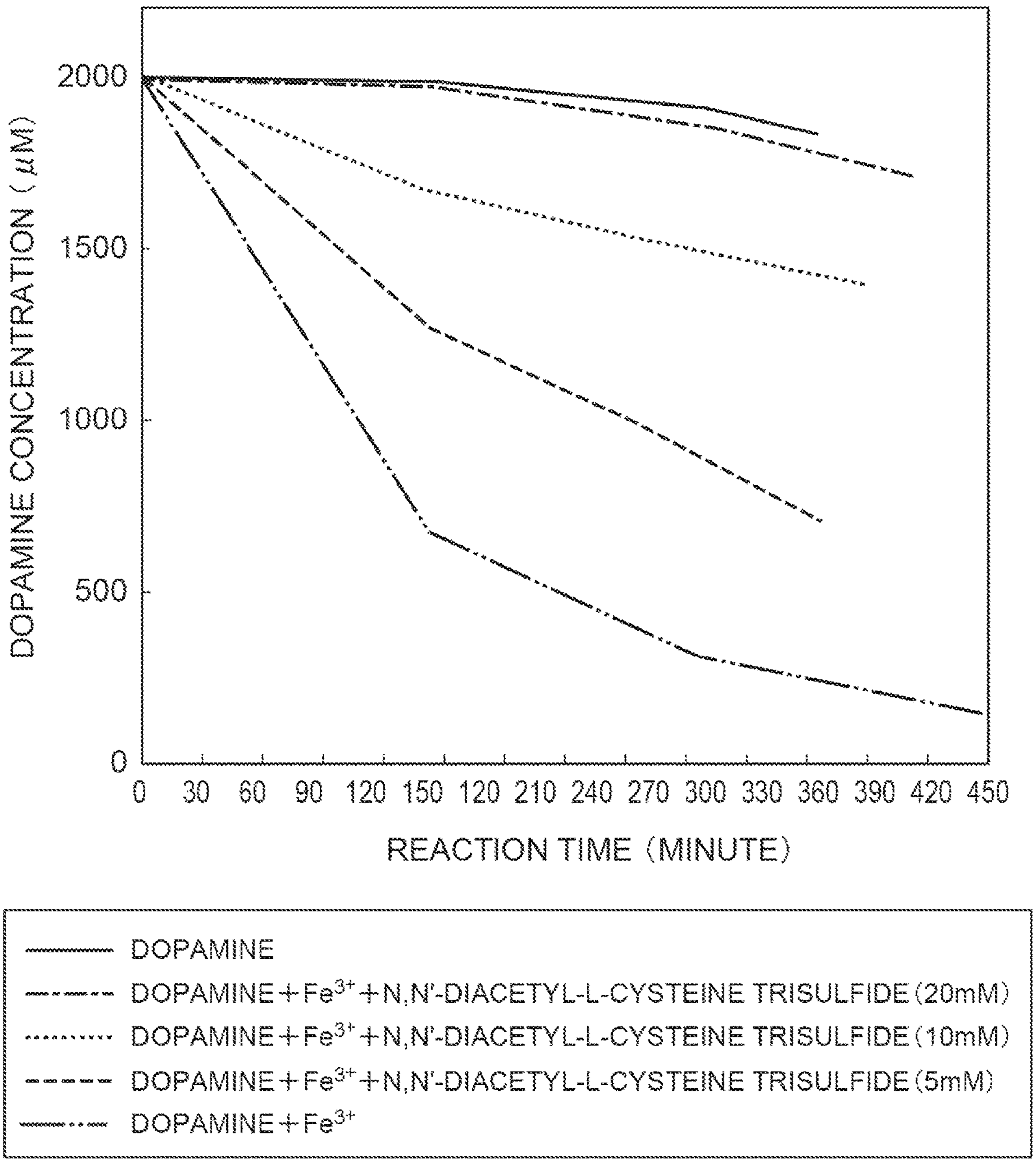
FIG. 4 is a graph showing that dopamine oxidation accelerated in the presence of iron ions is suppressed by N,N'-diacetyl-L-cysteine trisulfide.

Area measurement range: for 30 minutes after infusion of sample solution Preparation of sample solution: prepared by diluting 100 μL reaction solution 10-fold with water to form sample solution Retention time: Dopamine (DA) approximately 7 minutes As shown in FIG. 1, dopamine oxidation was accelerated in the presence of $Fe^{3+}$, and the dopamine concentration rapidly dropped. Glutathione trisulfide suppressed the dopamine oxidation in the presence of $Fe^{3+}$. Likewise, as shown in FIG. 2, lipoic acid trisulfide also suppressed the dopamine oxidation in the presence of $Fe^{3+}$. Likewise, as shown in FIG. 3, pantethine trisulfide also suppressed the dopamine oxidation in the presence of $Fe^{3+}$. Likewise, as shown in FIG. 4, N,N'-diacetyl-L-cysteine trisulfide also suppressed the dopamine oxidation in the presence of $Fe^{3+}$.

Since glutathione trisulfide, lipoic acid trisulfide, pantethine trisulfide and N,N'-diacetyl-L-cysteine trisulfide were effectively able to suppress dopamine oxidation reaction accelerated in the presence of $Fe^{3+}$, it is expected that the concurrent use of the drug with the conventional dopamine replacement therapy may effectively address the problems of conventional dopamine replacement therapy, the problems in which symptoms are not improved (wearing off), the effects of the drug suddenly run out (on-off phenomenon), side effects of the drug occur (dyskinesia, etc.) and the like.

Reference Example 1

Production of (R)-Lipoic Acid Trisulfide

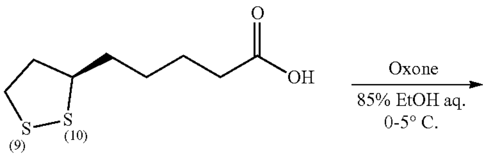

(R)-Lipoic acid

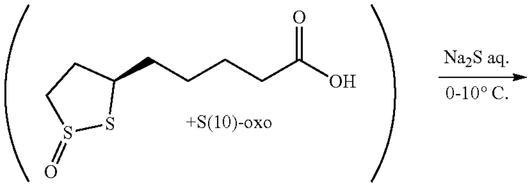

(R)-Lipoic acid sulfoxide

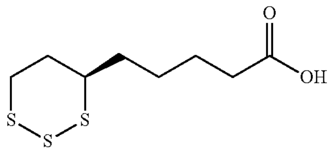

(R)-Lipoic acid trisulfide 24.38 g (118.17 mmol) of (R)-α-lipoic acid and 488 mL (20.0 v/w) of a 75% ethanol aqueous solution were added to a 200 mL four-neck flask. After confirming that the contents of the flask had dissolved, the internal temperature was cooled to 0° C. Oxone (registered trademark) (41.40 g, 124.20 mmol, 1.05 equivalents) was added thereto in two portions to cause a reaction for about 50 minutes. An insoluble substance in the reaction solution was removed by filtration and then washed with 65 mL (2.67 v/w) of ethanol. 400 mL (206.93 mmol, 1.75 equivalents) of a $Na_2S$ aqueous solution (70.70 g of $Na_2S \cdot 9H_2O$ dissolved in 569 mL of water) was added dropwise to the filtrate and wash liquid at an internal temperature of 2° C. to 6° C. over about 2.5 hours (during the dropwise addition and the reaction, a 3 mol/L sulfuric acid aqueous solution was used to control the pH at 6 to 7, and the total amount thereof used was 14 mL). After causing a reaction at an internal temperature of 3° C. at a pH 7 for about 50 minutes, 41 mL (1.7 v/w) of a 3 mol/L sulfuric acid aqueous solution was added dropwise thereto to adjust the pH to 1.3. Next, 320 mL (13.1 v/w) of water and 320 mL (13.1 v/w) of ethyl acetate were added thereto to perform extraction with ethyl acetate. The aqueous layer was extracted four times with 160 mL (6.6 v/w) of ethyl acetate, and organic layers were combined and concentrated under reduced pressure at an external temperature of 30° C. Ethanol was added to the concentrate to dissolve it, followed by column purification with ODS. The fraction was concentrated under reduced pressure at an external temperature of 30° C. and then dried with an oil pump to obtain 10.69 g of (R)-lipoic acid trisulfide (44.84 mmol, yield 38%, HPLC purity of 99.7%, white solid).

Production of (R)-Lipoamide Trisulfide

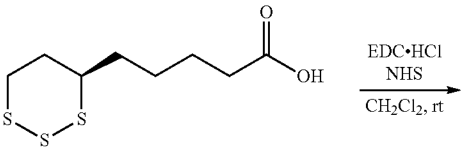

(R)-Lipoic acid trisulfide

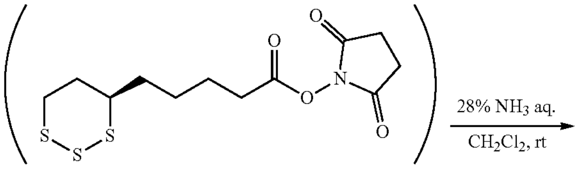

(R)-Lipoic acid trisulfide-NHS ester

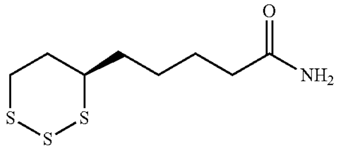

(R)-Lipoamide trisulfide 2.00 g (8.39 mmol) of (R)-lipoic acid trisulfide and 65 mL (32.5 v/w) of methylene chloride were added to a 200 mL four-neck flask. After confirming that the contents of the flask had dissolved, 2.07 g (10.77 mmol, 1.28 equivalents) of 1-(3-diinethylaminopropyl)-3-ethylcarbodiimide hydrochloride (EDC·HCl) and 1.42 g (12.33 mmol, 1.47 equivalents) of N-hydroxysuccinimide (NHS) were added thereto. After replacing the air in the flask with nitrogen, a reaction was carried out at room temperature for about 8 hours. Next, 2.28 mL (33.74 mmol, 4.02 equivalents) of 28% aqueous ammonia was added dropwise at room temperature over 5 minutes and allowed to react overnight. Thereafter, at room temperature, 60 mL of water (30.0 v/w) was added thereto and the mixture was subjected to liquid separation. Then, the organic layer was washed three times with 60 mL (30.0 v/w) of a 2.5% sodium hydrogen carbonate aqueous solution and additionally washed four times with 60 mL of water (30.0 v/w). Thereafter, the organic layer after washing was concentrated under reduced pressure at an external temperature of 25° C., and then dried with an oil pump to obtain 1.93 g of (R)-lipoamide trisulfide (8.13 mmol, yield 97%, HPLC purity of 99.6%, white solid).

$^1H$-NMR: ($CDCl_3$, 400 MHz) δ (ppm)=5.36 (bs, 2H), 3.33 (m, 1H), 3.13 (m, 2H), 2.22 (m, 3H), 1.89 (m, 1H), 1.74-1.42 (m, 6H).

HR-ESI-TOF-MS: m/z 236.0238 ($[M-H]^-$), calcd for $[C_8H_{14}NOS_3]$−236.0243.

Reference Example 2

Production of Lipoamide Trisulfide (Racemate)

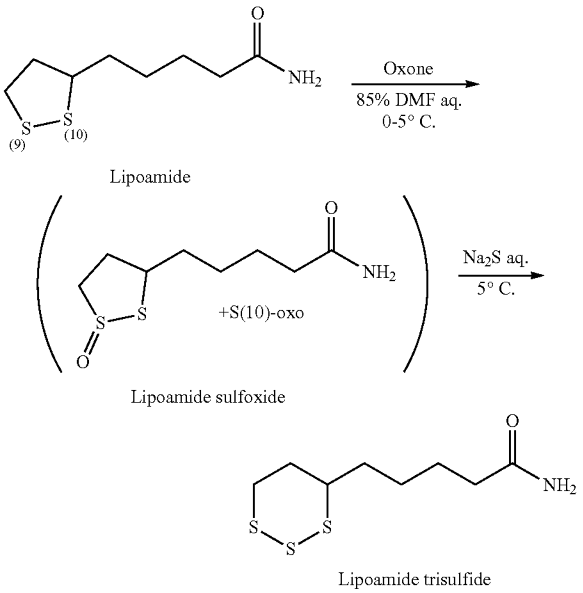

Lipoamide

Lipoamide sulfoxide

Lipoamide trisulfide 1.00 g (4.87 mmol) of lipoamide (racemate) and 182 mL (182.0 v/w) of an 85% dimethylformamide aqueous solution were added to a 500 mL four-neck flask. After confirming that the contents of the flask had dissolved, the internal temperature was cooled to 4° C. 1.63 g (4.89 mmol, 1.00 equivalent) of Oxone (registered trademark) was added to the flask in three portions every 10 minutes to cause a reaction for about 1 hour. 1.24 g (5.16 mmol, 1.06 equivalents) of sodium sulfide nonahydrate was added in portions at an internal temperature of 5° C. while controlling the pH of the reaction solution at 5 to 11 using a 3 mol/L sulfuric acid aqueous solution to cause a reaction for about 1.5 hours. 180 mL (180.0 v/w) of water and 50 mL (50.0 v/w) of methylene chloride were added thereto to perform extraction with methylene chloride. Then, the aqueous layer was extracted twice with 50 mL (50.0 v/w) of methylene chloride, and organic layers were combined and concentrated under reduced pressure at an external temperature of 30° C. or lower. 80 mL (80.0 v/w) of water was added dropwise to the concentrated residue over 30 minutes at room temperature for crystallization, and the slurry was filtered and then washed with 50 mL (50.0 v/w) of water. Wet crystals were dried under reduced pressure at 25° C. to obtain 510 mg of lipoamide trisulfide (racemate) (2.15 mmol, yield 44%, HPLC purity of 92%, white solid).

<Purity Test (HPLC) of Lipoamide Trisulfide>

Detector: Ultraviolet absorptiometer (measurement wavelength: 220 nm)

Column: LiChrosorb RP-18 (Kanto Chemical Co., Inc., 4.0 mm I.D.×250 mm, 5 μm)

Column temperature: Constant temperature around 40° C.

Mobile phase A: Phosphoric acid aqueous solution (pH 3)

Mobile phase B: Methanol

Mobile phase delivery: The mixing ratio of the mobile phase A and the mobile phase B was changed as follows to control the concentration gradient.

TABLE 1

| Time after injection (minute) | Mobile phase A (vol %) | Mobile phase B (vol %) |
|---|---|---|
| 0 to 5 | 100 | 0 |
| 5 to 15 | 100 → 25 | 0 → 75 |
| 15 to 20 | 25 | 75 |
| 20 to 21 | 25 → 100 | 75 → 0 |
| 21 to 35 | 100 | 0 |

Flow rate: 1 mL/min

Injection volume: 10 μL

Area measurement range: 35 minutes after injecting sample solution

Holding time: lipoamide sulfoxide (12 to 13 minutes), lipoamide (about 17 minutes), and lipoamide trisulfide (about 19 minutes)

Reference Examples 3 to 9

Hereinafter, "HP", "Me", and "Mal" are respectively abbreviations for "hydroxypropyl", "methyl", and "maltosyl."

<Production of Lipoic Acid Trisulfide>

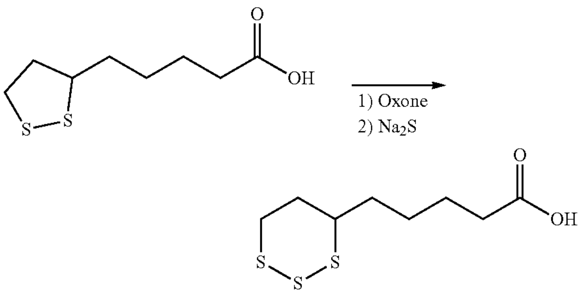

2.0 g (9.02 mmol) of lipoic acid and 40 mL of a 75% ethanol aqueous solution were added to a reaction container, and the mixture was cooled to an internal temperature of 0° C. 3.4 g (10.20 mmol) of Oxone (registered trademark) was added thereto to cause a reaction for about 2 hours. Inorganic salts in the reaction solution were filtered and then washed in 7 mL of ethanol. 5.8 g (24.1 mmol) of sodium sulfide nonahydrate was added to the filtrate to cause a reaction for about 1 hour. After 7 mL of a 3 mol/L sulfuric acid aqueous solution was added dropwise to this reaction solution, 20 mL of water and 45 mL of ethyl acetate (AcOEt) were subsequently added thereto to perform extraction with AcOEt. The aqueous layer was extracted twice with 20 mL of AcOEt, and organic layers were combined and concentrated under reduced pressure. After 3 mL of ethanol was added to the concentrate to dissolve it, the solution was purified with an ODS column (YMC Dispo PackAT, mobile phase: acetonitrile aqueous solution) to obtain 0.7 g (2.39 mmol, HPLC purity: 100%) of lipoic acid trisulfide.

<Production of CD Clathrate of Lipoic Acid Trisulfide>

Reference Example 3: β-CD Clathrate of Lipoic Acid Trisulfide (Racemate)

1,020.0 mg (0.899 mmol) of β-CD and 80 mL of water were added to a 100 mL eggplant flask. After confirming that the contents of the flask had dissolved, 99.8 mg (0.419 mmol) of lipoic acid trisulfide was added thereto, and the inside of the flask was washed with 20 mL of water. The washed mixture was stirred at 45° C. for 15 minutes and then filtered, and the inside of the flask and the crystals were washed with 10 mL of water. The obtained filtrate was frozen in a −20° C. freezer for 23 hours. The frozen filtrate was freeze-dried at an external temperature of 20° C. for about 4.5 days to obtain 980.0 mg of a clathrate (white solid).

Reference Example 4: HP-β-CD Clathrate of Lipoic Acid Trisulfide (Racemate)

1291.0 mg of HP-β-CD and 16 mL of water were added to a 50 mL eggplant flask. After confirming that the contents of the flask had dissolved, 100.0 mg (0.419 mmol) of lipoic acid trisulfide was added thereto. The mixture was stirred at room temperature for about 28 hours and then filtered, and the inside of the flask and the crystals were washed with 10 mL of water. The obtained filtrate was frozen in a −20° C. freezer for about 2 days. The frozen filtrate was freeze-dried at an external temperature of 20° C. for about 2 days to obtain 1330.0 mg of a clathrate (white solid).

Reference Example 5: HP-β-CD Clathrate of (R)-Lipoic Acid Trisulfide 969.9 mg of HP-β-CD and 10 mL of water were added to a 50 mL eggplant flask. After confirming that the contents of the flask had dissolved, 100.3 mg (0.421 mmol) of (R)-lipoic acid trisulfide was added thereto, and the inside of the flask was washed with 4 mL of water. The washed mixture was stirred at room temperature for about 25 hours and then filtered, and the inside of the flask and the crystals were washed with 12 mL of water. The obtained filtrate was frozen in a −20° C. freezer for 15 hours. The frozen filtrate was freeze-dried at an external temperature of 20° C. for about 2 days to obtain 1040.0 mg of a clathrate (white solid).

Reference Example 6: Me-β-CD Clathrate of Lipoic Acid Trisulfide (Racemate)

1,616.0 mg of Me-β-CD (mixture of several methylated) and 12 mL of water were added to a 50 mL eggplant flask. After confirming that the contents of the flask had dissolved, 101.0 mg (0.424 mmol) of lipoic acid trisulfide was added thereto, and the inside of the flask was washed with 4 mL of water. The washed mixture was stirred for 21 hours and then filtered, and the inside of the flask and the crystals were washed with 12 mL of water. The obtained filtrate was frozen in a −20° C. freezer for 20 hours. The frozen filtrate was freeze-dried at an external temperature of 20° C. for about 4 days to obtain 1665.2 mg of a clathrate (white solid).

Reference Example 7: ME-β-CD Clathrate of (R)-Lipoic Acid Trisulfide 1,616.0 mg of Me-β-CD (mixture of several methylated) and 16 mL of water were added to a 50 mL eggplant flask. After confirming that the contents of the flask had dissolved, 99.9 mg (0.420 mmol) of (R)-lipoic acid trisulfide was added thereto, and the inside of the flask was washed with 4 mL of water. The washed mixture was stirred at room temperature for about 6 hours and then filtered, and the inside of the flask and the crystals were washed with 13 mL of water. The obtained filtrate was frozen in a −20° C. freezer for 28 hours. The frozen filtrate was freeze-dried at an external temperature of 20° C. for about 3 days to obtain 1610.9 mg of a clathrate (white solid).

Reference Example 8: Mal-β-CD Clathrate of Lipoic Acid Trisulfide (Racemate)

1,224.2 mg (0.839 mmol) of Mal-β-CD and 14 mL of water were added to a 50 mL eggplant flask. After confirming that the contents of the flask had dissolved, 100.4 mg (0.421 mmol) of lipoic acid trisulfide was added thereto, and the inside of the flask was washed with 2 mL of water. The washed mixture was stirred at room temperature for about 31 hours and then filtered, and the inside of the flask and the crystals were washed with 10 mL of water. The obtained filtrate was frozen in a −20° C. freezer for 22 hours. The frozen filtrate was freeze-dried at an external temperature of 20° C. for about 46 hours to obtain 1180.0 mg of a clathrate (white solid).

Reference Example 9: Mal-β-CD Clathrate of (R)-Lipoic Acid Trisulfide 1,224.2 mg (0.839 mmol) of Mal-β-CD and 10 mL of water were added to a 50 mL eggplant flask. After confirming that the contents of the flask had dissolved, 100.1 mg (0.420 mmol) of (R)-lipoic acid trisulfide was added thereto, and the inside of the flask was washed with 5 mL of water. The washed mixture was stirred at room temperature for about 4.5 hours and then filtered, and the inside of the flask and the crystals were washed with 11 mL of water. The obtained filtrate was frozen in a −20° C. freezer for 24 hours. The frozen filtrate was freeze-dried at an external temperature of 20° C. for about 41 hours to obtain 1319.6 mg of a clathrate (white solid).

The yield and solubility of the clathrates obtained in Reference Examples 3 to 9 are shown in Table 2.

TABLE 2

| | Lipoic acid trisulfide | | β-CD | | Clathrate (freeze-dried product) | | | |
|---|---|---|---|---|---|---|---|---|
| | | | | Charge | Percent | Content (%) | | |
| Example | Type | Solubility (g/L[1)]) | Modification | amount (w/w) | yield (%)[2)] | Actual measurement | Theoretical value | Solubility (g/L[3)]) |
| 6 | Racemate | 0.1 | None | 10.2 | 84 | 8.6 | 8.9 | 0.77 |
| 7 | Racemate | 0.1 | HP | 12.9 | 94 | 7.1 | 7.2 | ≥49 |
| 8 | R. body | 0.3 | | 9.7 | 99 | 9.6 | 9.4 | ≥65 |

TABLE 2-continued

| | Lipoic acid trisulfide | | β-CD | | Clathrate (freeze-dried product) | | | |
|---|---|---|---|---|---|---|---|---|
| | | | | Charge | Percent | Content (%) | | |
| Example | Type | Solubility (g/L[1)]) | Modification | amount (w/w) | yield (%)[2)] | Actual measurement | Theoretical value | Solubility (g/L[3)]) |
| 9 | Racemate | 0.1 | Me | 16.0 | 96 | 5.8 | 5.9 | ≥50 |
| 10 | R body | 0.3 | | 16.2 | 99 | 6.1 | 5.8 | ≥41 |
| 11 | Racemate | 0.1 | Mal | 12.2 | 88 | 7.5 | 7.6 | ≥45 |
| 12 | R body | 0.3 | | | 105 | 8.0 | 7.6 | ≥52 |

[1)]represents solubility in water at 20° C.

[2)]Percent yield (%) = (yield x content)/theoretical yield x 100

[3)]represents solubility of lipoic acid trisulfide in a clathrate in water at 20° C. A statement such as "≥49 g/L" indicates dissolution at 49 g/L.

Reference Example 10

Production of Pantethine Trisulfide

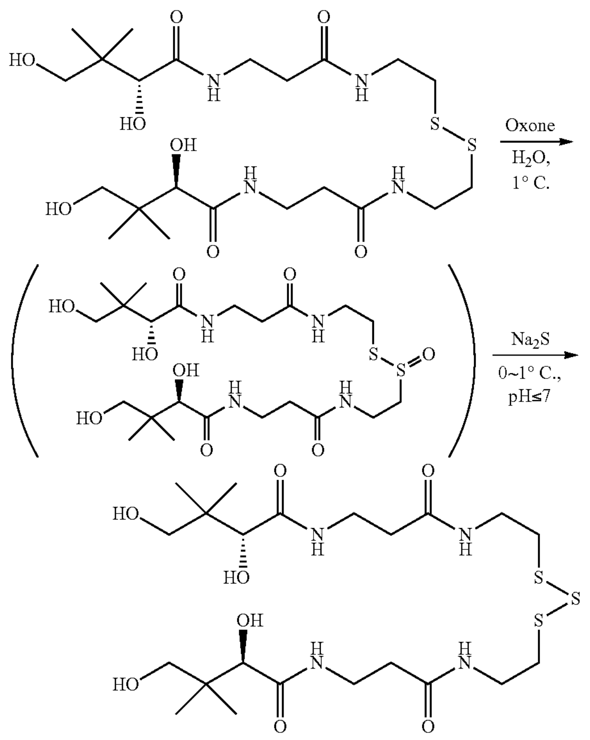

After charging 18.75 g (27.04 mmol, 15.00 g as pantethine) of a 80% pantethine aqueous solution and 180 ml (12.0 v/w) of water to a 1 L four-neck flask, the internal temperature was cooled to 1° C. 10.34 g of Oxone (registered trademark) (31.02 mmol, 1.15 equivalents, calculated as available oxygen of 4.8%) was added thereto in 4 portions every 10 minutes, and then the flask was washed with 8 mL of water and a reaction was carried out for about 3 hours. 45 mL of a 0.67 mol/L sodium sulfide aqueous solution (29.98 mmol, 1.11 equivalents) was added dropwise thereto over 45 minutes at an internal temperature of 0° C. to 1° C., and the pH was controlled at 7 or lower during dropwise addition using 1.6 mL of a 3 mol/L sulfuric acid aqueous solution. After the mixture was allowed to react at an internal temperature of 1° C. and at pH 4 for 40 minutes, 500 mL (33.3 v/w) of ethanol was added thereto at an internal temperature of 1° C. to 5° C. to precipitate inorganic salts, and then the resultant was stirred at an internal temperature of 1° C. to 5° C. for 30 minutes. The inorganic salts were filtered and then washed with 50 mL (3.3 v/w) of ethanol, and the filtrate and wash liquid were concentrated under reduced pressure at an external temperature of 23° C. to obtain 34 g of a crude body of pantethine trisulfide. Then, the crude body was dissolved by charging 6 mL of water thereto, and 40 g (2.7 w/w) of a stock solution for column purification was prepared. Purification was performed using an ODS column, and fractions with an LC purity of 95% or higher were collected. The fractions were concentrated under reduced pressure at an external temperature of 30° C. and then dried with an oil pump to obtain 9.57 g of pantethine trisulfide (16.31 mmol, yield 60%, white solid).

$^1H$ NMR: ($D_2O$, 400 MHz) δ (ppm)=3.97 (s, 2H), 3.44-3.58 (m, 10H), 3.37 (d, J=11.4 Hz, 2H), 3.04 (t, J=6.2 Hz, 4H), 2.50 (t, J=6.2 Hz, 4H), 0.91 (s, 6H), 0.87 (s, 6H).

HR-ESF-TOF-MS: m/z 585.2086 ($[M-H]^-$), calcd for $[C_{22}H_{41}N_4O_8S_3]$-585.2092.

<Purity Test for Pantethine Trisulfide>

Detector: Ultraviolet absorptiometer (measurement wavelength: 220 nm)

Column: LiChrosorb RP-18 (Kanto Chemical Co., Inc., 4.0 mm I.D.×250 mm, 5 μm)

Column temperature: Constant temperature around 40° C.

Mobile phase A: Phosphoric acid aqueous solution (pH 3)

Mobile phase B: Methanol

Mobile phase delivery: The mixing ratio of the mobile phase A and the mobile phase B was changed as follows to control the concentration gradient.

TABLE 3

| Time after injection (minute) | Mobile phase A (vol %) | Mobile phase B (vol %) |
|---|---|---|
| 0 to 5 | 100 | 0 |
| 5 to 15 | 100 → 50 | 0 → 50 |
| 15 to 40 | 50 | 50 |
| 40 to 41 | 50 → 100 | 50 → 0 |
| 41 to 50 | 100 | 0 |

Flow rate: 0.6 mL/min

Injection volume: 5 μL

Area measurement range: 40 minutes after injecting sample solution

Retention time: pantethine sulfoxide (about 20 minutes), pantethine (about 22 minutes), pantethine trisulfide (about 23 minutes)

Reference Example 11: Nasal Drop Formulation of Pantethine Trisulfide (10%)

Pantethine trisulfide (10% by mass), benzalkonium (0.01% by mass), carboxyvinyl polymer (0.5% by mass), L-arginine (1% by mass), and physiological saline (88.49% by mass) were mixed and stirred in a vacuum stirrer under shade, filtered and sterilized under sterile conditions, and aseptically filled in a sterilized container to produce a nasal drop formulation comprising pantethine trisulfide.

Reference Example 12: Production of N,N'-Diacetyl-L-Cysteine Trisulfide

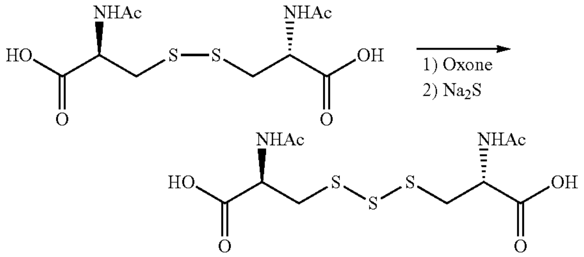

1.0 g (3.08 mmol) of N,N'-diacetyl-L-cystine and 10 mL of water were added to a reaction container, and the mixture was cooled to an internal temperature of 1° C. 1.25 g (3.72 mmol) of Oxone (registered trademark) was added thereto to cause a reaction for about 3 hours. Subsequently, 8.5 mL (3.71 mmol) of a 0.44 mol/L sodium sulfide aqueous solution was added dropwise thereto to cause a reaction for about 3 hours. After adding 33 mL of acetonitrile to the reaction mixture, inorganic salts were filtered and washed with 5 mL of acetonitrile. This filtrate was concentrated under reduced pressure with an evaporator, and the concentrate was purified with an ODS column (mobile phase: acetonitrile aqueous solution) to give 0.2 g (0.56 mmol) of N,N'-diacetyl-L-cysteine trisulfide.

The HPLC conditions are as follows.

Detector: Ultraviolet absorptiometer (measurement wavelength: 220 nm)

Column: LiChrosorb RP-18 (Kanto Chemical Co., Inc., 4.0×250 mm, 5 μm)

Column temperature: Constant temperature around 40° C.

Mobile phase: 40% (v/v) Acetonitrile aqueous solution

Flow rate: 0.5 mL/min

Reference Example 13: Production of N,N'-Diacetyl-L-Cysteine Trisulfide

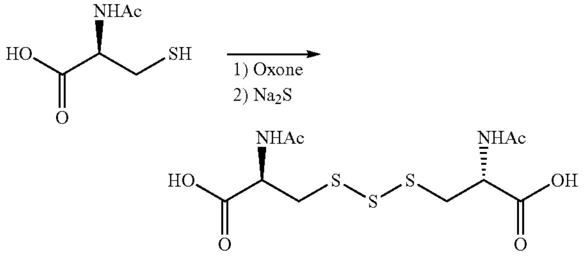

1.0 g (6.13 mmol) of N-acetyl-L-cystine and 40 mL of a 20% acetonitrile aqueous solution were added to a reaction container, and the mixture was cooled to an internal temperature of 5° C. 3.4 g (10.14 mmol) of Oxone (registered trademark) was added thereto to cause a reaction for about 2.5 hours. Subsequently, 1.5 g (6.12 mmol) of sodium sulfide nonahydrate was added thereto to cause a reaction for about 1 hour. After adding 33 mL of acetonitrile thereto, inorganic salts were filtered and washed with 3 mL of acetonitrile. This filtrate was concentrated under reduced pressure with an evaporator, and the concentrate was purified with an ODS column (mobile phase: acetonitrile aqueous solution) to give 0.1 g (0.28 mmol) of N,N'-diacetyl-L-cysteine trisulfide.

HPLC conditions are the same as those described in Reference Example 12.

The invention claimed is:

1. A method for suppressing dopamine decomposition comprising administering (i) a trisulfide compound and (ii) a drug utilized in dopamine replacement therapy or a pharmaceutically acceptable salt thereof to a patient having Parkinson's disease, wherein the trisulfide compound is
   (a) glutathione trisulfide or a pharmaceutically acceptable salt thereof,
   (b) lipoic acid trisulfide or a pharmaceutically acceptable salt thereof or a cyclodextrin clathrate thereof,
   (c) pantethine trisulfide or a pharmaceutically acceptable salt thereof, or
   (d) N,N'-diacetyl-L-cysteine trisulfide or a pharmaceutically acceptable salt thereof.

2. The method according to claim 1, wherein the trisulfide compound is glutathione trisulfide or a pharmaceutically acceptable salt thereof.

3. The method according to claim 2, wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

4. The method according to claim 2, wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

5. The method according to claim 1, wherein the trisulfide compound is lipoic acid trisulfide or a pharmaceutically acceptable salt thereof.

6. The method according to claim 1, wherein the trisulfide compound is pantethine trisulfide or a pharmaceutically acceptable salt thereof.

7. The method according to claim 1, wherein the trisulfide compound is N,N'-diacetyl-L-cysteine trisulfide or a pharmaceutically acceptable salt thereof.

8. The method according to claim 1, wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

9. A kit for suppressing dopamine decomposition in a patient having Parkinson's disease, wherein the kit comprises (i) a formulation comprising a trisulfide compound and (ii) a formulation comprising a drug utilized in dopamine replacement therapy or a pharmaceutically acceptable salt thereof, wherein the trisulfide compound is
   (a) glutathione trisulfide or a pharmaceutically acceptable salt thereof, (b) lipoic acid trisulfide or a pharmaceutically acceptable salt thereof or a cyclodextrin clathrate thereof, (c) pantethine trisulfide or a pharmaceutically acceptable salt thereof, or (d) N,N'-diacetyl-L-cysteine trisulfide or a pharmaceutically acceptable salt thereof.

10. The kit according to claim 9, wherein the trisulfide compound is glutathione trisulfide or a pharmaceutically acceptable salt thereof.

11. The kit according to claim 10, wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

12. The kit according to claim 10, wherein the glutathione trisulfide or a pharmaceutically acceptable salt thereof comprises at least one selected from the group consisting of glutathione trisulfide, an arginine salt of glutathione trisulfide, and a sodium salt of glutathione trisulfide.

13. The kit according to claim 9, wherein the trisulfide compound is lipoic acid trisulfide or a pharmaceutically acceptable salt thereof.

14. The kit according to claim 9, wherein the trisulfide compound is pantethine trisulfide or a pharmaceutically acceptable salt thereof.

15. The kit according to claim 9, wherein the trisulfide compound is N,N'-diacetyl-L-cysteine trisulfide or a pharmaceutically acceptable salt thereof.

16. The kit according to claim 9, wherein the drug used for dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

17. A pharmaceutical composition for suppressing dopamine decomposition in a patient having Parkinson's disease comprising (i) a trisulfide compound and (ii) a drug utilized in dopamine replacement therapy or a pharmaceutically acceptable salt thereof, wherein the trisulfide compound is (a) glutathione trisulfide or a pharmaceutically acceptable salt thereof, (a} glutathione trisulfide or a pharmaceutically acceptable salt thereof, (b) lipoic acid trisulfide or a pharmaceutically acceptable salt thereof or a cyclodextrin clathrate thereof, (c) pantethine trisulfide or a pharmaceutically acceptable salt thereof, or (d) N,N'-diacetyl-L-cysteine trisulfide or a pharmaceutically acceptable salt thereof.

18. The composition according to claim 17, wherein the trisulfide compound is glutathione trisulfide or a pharmaceutically acceptable salt thereof.

19. The composition according to claim 18, wherein the glutathione trisulfide or a pharmaceutically acceptable salt thereof comprises at least one selected from the group consisting of glutathione trisulfide, an amino acid salt of glutathione trisulfide, and an alkali metal salt of glutathione trisulfide.

20. The composition according to claim 17, wherein the drug utilized in dopamine replacement therapy comprises at least one selected from the group consisting of a dopamine precursor, a dopa-decarboxylase inhibitor, a catechol-O-methyltransferase inhibitor, a monoamine oxidase inhibitor, a dopamine release accelerator, and a dopamine agonist.

* * * * *